(12) United States Patent
Yamashita et al.

(10) Patent No.: US 9,113,633 B2
(45) Date of Patent: Aug. 25, 2015

(54) CALCIUM HYPOCHLORITE COMPOSITION

(75) Inventors: Toshiyuki Yamashita, Toride (JP); Yoshinori Kamatsuchi, Joetsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/128,223

(22) PCT Filed: Jun. 21, 2012

(86) PCT No.: PCT/JP2012/065922
§ 371 (c)(1),
(2), (4) Date: Dec. 20, 2013

(87) PCT Pub. No.: WO2013/002128
PCT Pub. Date: Jan. 3, 2013

(65) Prior Publication Data
US 2014/0134278 A1   May 15, 2014

(30) Foreign Application Priority Data
Jun. 28, 2011 (JP) .................................. 2011-143477

(51) Int. Cl.
*A01N 59/06* (2006.01)
*A01N 59/00* (2006.01)
*C02F 1/50* (2006.01)

(52) U.S. Cl.
CPC ............... *A01N 59/06* (2013.01); *A01N 59/00* (2013.01); *C02F 1/50* (2013.01)

(58) Field of Classification Search
CPC ............ C02F 1/50; A01N 59/06; A01N 59/00
USPC ........................................................ 424/665
See application file for complete search history.

(56) References Cited

U.S. PATENT DOCUMENTS

| | | | |
|---|---|---|---|
| 3,793,216 A | 2/1974 | Dychdala et al. | |
| 4,780,216 A * | 10/1988 | Wojtowicz | 210/756 |
| 5,350,511 A | 9/1994 | Sakurada | |
| 2005/0025809 A1 * | 2/2005 | Hasirci et al. | 424/426 |
| 2006/0276338 A1 * | 12/2006 | Hodgetts et al. | 504/116.1 |

FOREIGN PATENT DOCUMENTS

| | | |
|---|---|---|
| CN | 1113889 A | 12/1995 |
| CN | 2625384 Y | 7/2004 |
| JP | 59-13890 B2 | 4/1984 |
| JP | 63-030304 A | 2/1988 |
| JP | 63-179809 A | 7/1988 |
| JP | 02-500256 A | 1/1990 |
| JP | 03-012289 A | 1/1991 |
| JP | 04-500171 A | 1/1992 |
| JP | 06-501418 A | 2/1994 |
| JP | 08-155465 A | 6/1996 |
| JP | 11-505245 A | 5/1999 |
| JP | 2000-500815 A | 1/2000 |
| JP | 2006-521995 A | 9/2006 |
| JP | 2006-522805 A | 10/2006 |
| JP | 2009-544802 A | 12/2009 |
| WO | WO 88/00928 A1 | 2/1988 |
| WO | WO 90/01979 A1 | 3/1990 |
| WO | WO 91/11392 A1 | 8/1991 |
| WO | WO 92/06926 A1 | 4/1992 |
| WO | WO 96/36566 A1 | 11/1996 |
| WO | WO 98/06814 A1 | 2/1998 |
| WO | WO 2004/089081 A2 | 10/2004 |
| WO | WO 2004/093847 A1 | 11/2004 |
| WO | WO 2006/093556 A2 | 9/2006 |
| WO | WO 2008/013746 A1 | 1/2008 |

OTHER PUBLICATIONS

Office Action mailed Nov. 4, 2014, in JP 2013-522807 with English translation.
Office Action mailed Sep. 10,2014, in CN 201280030957.X with English translation.
International Search Report dated Aug. 14, 2012, in PCT/JP2012/065922.
Edited by Pesticide Science Society of Japan Noyaku Seizai, Shiyoho Kenkyukai, Noyaku Seizei Guide, Japan Plant Protection Association, 1997, pp. 2-7, pp. 129-135, p. 3, table 1, p. 131, '(3) Asshuku Zoryuki', p. 133, '(1) Asshuku Seikeiki.'

* cited by examiner

*Primary Examiner* — Blessing M Fubara
(74) *Attorney, Agent, or Firm* — Foley & Lardner LLP

(57) ABSTRACT

The present invention provides a composition containing an aluminate and calcium hypochlorite, wherein the content of the aluminate is 1.0 part by weight to less than 2 parts by weight based on 100 parts by weight of the composition.

6 Claims, 2 Drawing Sheets

CALCIUM HYPOCHLORITE COMPOSITION

CROSS-REFERENCE TO RELATED APPLICATIONS

This application is a National Stage application of PCT/JP2012/065922, filed Jun. 21, 2012, which claims priority from Japanese patent application JP 2011-143477, filed Jun. 28, 2011.

TECHNICAL FIELD

The present invention relates to a composition containing calcium hypochlorite preferable for use as a pool water disinfectant and the like.

The present application claims priority on the basis of Japanese Patent Application No. 2011-143477 filed in Japan on Jun. 28, 2011, the contents of which are incorporated herein by reference.

BACKGROUND ART

Calcium hypochlorite, water-soluble zinc salts and coagulants that can be mixed safely with the two are known as compositions for disinfecting pools or spas and the like and inhibiting algae growth therein (see Patent Document 1).

A specific example of a coagulant is sodium aluminate, while specific examples of disclosed compositions include a composition containing 80 g of calcium hypochlorite, 10 g of zinc sulfate monohydrate and 10 g of sodium aluminate, and a composition containing 90 g of calcium hypochlorite, 5 g of zinc sulfate monohydrate and 5 g of sodium aluminate. Furthermore, a coagulant refers to that which has a function that coagulates particles dispersed in contaminated water and promotes precipitation thereof.

PRIOR ART DOCUMENTS

Patent Documents

[Patent Document 1] International Publication No. WO 2006-093556

DISCLOSURE OF THE INVENTION

Problems to be Solved by the Invention

Although the aforementioned composition is used by placing in a special container capable of floating in a pool and the like, in a pool having a circulating filtration mechanism, a large amount of dissolution residue remained in the container resulting in the problem of the container becoming clogged in the case of using by placing in a container installed at an intermediate location in the circulation path.

An object of the present invention is to provide a composition that allows the obtaining of water clarity without causing clogging even in the case of using by placing in a container installed at an intermediate location in a circulation path in a pool having a circulating filtration mechanism.

Means for Solving the Problems

As a result of conducting extensive studies to achieve the aforementioned object, the inventors of the present invention found that, by using a certain specified amount of an alkaline metal aluminate, adequate clarity can be secured without clogging even in the case of using the aforementioned container, thereby leading to completion of the present invention.

Namely, the present invention includes that indicated below.

(1) A composition supplied for use in a swimming pool having a circulating filtration mechanism, comprising: an aluminate and calcium hypochlorite.

(2) The composition described in (1) above, wherein the content of the aluminate is 1.0 part by weight to less than 2 parts by weight based on 100 parts by weight of the composition.

(3) The composition described in (1) above, wherein the content of the aluminate is 1.0 part by weight to 1.5 parts by weight based on 100 parts by weight of the composition.

(4) The composition described in any of (1) to (3) above, wherein the aluminate is sodium aluminate.

(5) The composition described in any of (1) to (4) above, wherein the usage form of the composition is a tablet.

(6) The composition described in any of (1) to (5) above, which is provided in a container installed in a swimming pool having a circulating filtration mechanism.

(7) A method for producing a disinfectant for a swimming pool having a circulating filtration mechanism, comprising: dry molding a composition containing an aluminate and calcium hypochlorite.

(8) The production method described in (7) above, wherein the dry molding consists of tableting or pelleting with a briquette machine.

Effects of the Invention

The composition of the present invention is preferably used as a water disinfectant capable of effectively disinfecting circulating pool water particularly in the case of using in the form of a tablet. In addition, since the aluminate is a basic salt, it has superior storage stability even in the case of using in the form of a preparation obtained by mixing with a calcium hypochlorite composition. Moreover, since the aluminate has a high concentration as aluminum, it demonstrates water purifying effects even in small amounts, and as a result thereof, enables the content of calcium hypochlorite to be relatively high.

BEST MODE FOR CARRYING OUT THE INVENTION

The composition of the present invention is provided for use in a swimming pool having a circulating filtration mechanism, and comprises an aluminate and calcium hypochlorite.

Figure 1:
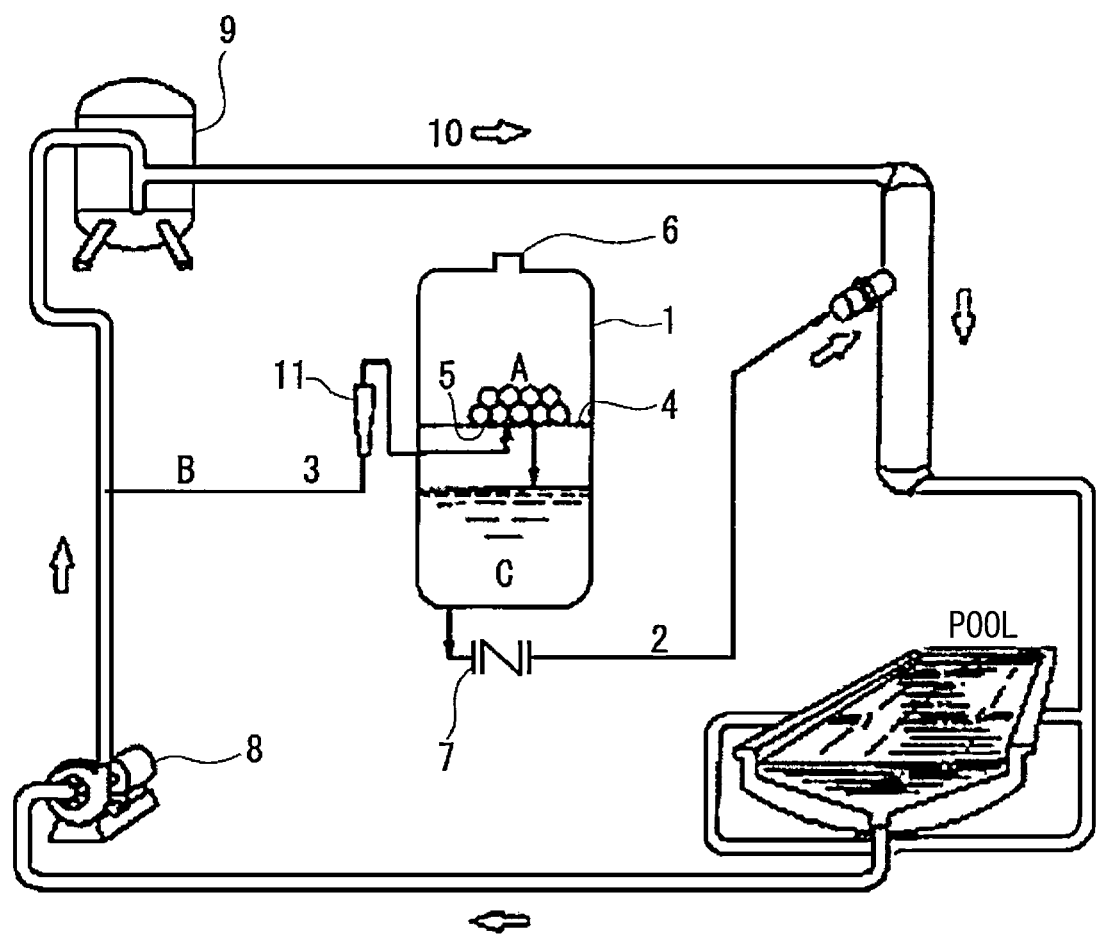
FIG. 1 depicts a specific example of a swimming pool having a circulating filtration mechanism.

As shown in FIG. 1, an example of a pool having a circulating filtration mechanism is a solid chemical agent dissolving apparatus system having a chemical agent dissolving tank 1 filled with a solid chemical agent A, a main treated water pipe 2, a pipe 3 for supplying water B to the chemical agent dissolving tank, a perforated plate 4 that holds the filled layer of the solid chemical agent A in the chemical agent dissolving tank 1 above the water level of chemical agent dissolved water C, a spray nozzle 5 that sprays upward water supplied into the chemical agent dissolving tank 1, a solid chemical agent addition port 6, a check valve (non-return valve) 7, a pump 8 for circulating filtration of pool water, a filtration machine 9 for filtering pool water, circulating pool water 10, and a flow meter 11 for controlling the amount of water in which the chemical agent is dissolved. Furthermore, in a swimming pool having a circulating filtration mechanism, the presence or absence of the installation of a solid chemical agent dissolving apparatus, the installation site, details of the structure of the solid chemical agent dissolving apparatus and the locations of pipes are not limited to that shown in FIG. 1. Aluminates demonstrate coagulating effects and have the effect of improving water clarity. Examples of applicable circulating filtration machines include cartridge-type filtration machines, diatomaceous earth-type filtration machines and sand filtration machines. Among these, sand filtration machines are the most preferable. Furthermore, these filtration machines do not impair the combined use of an ozone sterilizer or ultraviolet sterilizer.

The calcium hypochlorite used in the present invention is a compound represented by the chemical formula $Ca(ClO)_2$. There are no particular limitations on this calcium hypochlorite provided it is used as a main component of disinfectants. Calcium hypochlorite is thought to be in a state of dissociation equilibrium between hypochlorous acid and calcium hydroxide in water. Hypochlorous acid is able to disinfect water by eradicating microorganisms in the water such as *Escherichia coli*, adenovirus type 3 (causative organism of pharyngoconjunctival fever), *Entamoeba histolytica*, aerobic bacilli, *Salmonella typhi*, coxsackievirus type A2 (causative organism of aseptic meningitis) or *Bacillus anthracis*.

The content of the calcium hypochlorite is preferably 59 parts by weight to 73.5 parts by weight, and more preferably 63 parts by weight to 72.8 parts by weight, based on 100 parts by weight of the composition.

There are no particular limitations on the aluminate used in the present invention. A preferable example thereof is sodium aluminate. In addition, other examples include complex oxides such as sodium aluminum dioxide ($NaAlO_2$) and hydroxo complexes such as sodium tetrahydroxoaluminate ($Na[Al(OH)_4]$).

Aluminum oxide and aluminum hydroxide are referred to as being amphoteric in that they form salts containing aluminum ions when reacting with acid, and form aluminates when reacting with strong base. Aluminates can be produced by reacting an aluminum compound such as aluminum, aluminum oxide or aluminum hydroxide with a strong base such as sodium hydroxide or sodium carbonate.

Sodium aluminum dioxide is formed when a mixture of aluminum oxide and sodium carbonate melts at high temperatures.

Although sodium aluminum dioxide formally has the chemical formula $NaAlO_2$ equivalent to the sodium salt of an oxo acid in the form of aluminic acid ($HAlO_2$), since independent aluminic acid ions ($AlO_2^-$) are not found in crystals, it should be referred to as a complex oxide of sodium and aluminum. In crystals of the 5/4 hydrate ($NaAlO_2 \cdot 5/4H_2O$), aluminum atoms exhibit a tetrahedral tetracoordination and are surrounded by four oxygen atoms. Although pure sodium aluminum dioxide is in the form of colorless crystals or a white solid, industrial quality products have a yellowish-brown tint as a result of containing impurities such as iron. Sodium aluminum dioxide is deliquescent, extremely soluble in water, and forms an aqueous solution of sodium tetrahydroxoaluminate when dissolved in water. This aqueous solution demonstrates strong basicity due to hydrolysis, and easily undergoes hydrolysis even in the presence of a weak acid such as carbonic acid, resulting in precipitation of aluminum hydroxide. Sodium aluminum hydroxide is also susceptible to deterioration as a result of absorbing moisture and carbon dioxide in the air.

Sodium tetrahydroxoaluminate is formed by dissolving aluminum metal and aluminum hydroxide in an aqueous sodium hydroxide solution.

Although present in a solution obtained by dissolving aluminum and aluminum hydroxide in an aqueous sodium hydroxide solution, it is difficult to isolate the sodium tetrahydroxoaluminate as a solid. The aqueous solution demonstrates strong basicity as a result of hydrolysis, and easily undergoes hydrolysis resulting in precipitation of aluminum hydroxide. Sodium tetrahydroxoaluminate is stabilized with respect to hydrolysis by the presence of an organic compound having hydroxyl groups. The presence of the tetrahedral form $[Al(OH)_4]^-$ has been indicated at low concentrations in a strongly basic aqueous solution according to $^{27}Al$-NMR, infrared spectroscopy, Raman spectroscopy and ion exchange, while the presence of $[(HO)_3AlOAl(OH)_3]^{2-}$ having a crosslinked Al—O—Al structure has been confirmed at high concentrations.

Although there are no particular limitations thereon, the content of the aluminate is preferably within the range of 1.0 part by weight to less than 2.0 parts by weight, and more preferably within the range of 1.0 part by weight to 1.5 parts by weight, based on 100 parts by weight of the composition from the viewpoints of coagulation performance, form of the chemical agent and dissolution rate. Furthermore, in the case the aluminate concentration is less than 1.0 part by weight based on 100 parts by weight of the composition, clarity of the water is inadequate due to insufficient content. Conversely, in the case the aluminate concentration is 2.0 parts by weight or more, the amount of dissolution residue increases, thereby impairing continuous use.

In addition, the effective amount of chlorine consumption in a pool differs considerably between indoor pools and outdoor pools, and in the case of a pool having a capacity of 300 $m^3$, in contrast to effective chlorine consumption in an indoor pool being about 600 g/day, since that in the case of an outdoor pool on clear day in summer is 3 kg/day, the content of the aluminate is determined in consideration of this effective chlorine consumption.

In the case of water disinfectant compositions containing aluminum sulfate as an assistant, and particularly in the case of tablets of these compositions, calcium ions of the calcium hypochlorite react with sulfate ions when dissolved in water resulting in the formation of calcium sulfate (gypsum). In contrast, in the composition of the present invention, since calcium ions and aluminic acid ions do not react directly when dissolved, hydroxide ions formed by hydrolysis of aluminic acid ions react with calcium ions, resulting only in the formation of calcium hydroxide. Since the calcium hydroxide may be used as an unreacted substance in the production process of calcium hypochlorite, or as a substance used for the purpose of stabilizing the calcium hypochlorite or adjusting the dissolution rate of the chemical agent, production of the calcium hydroxide by-product does not present a problem. Since the aluminate and calcium hypochlorite react quantitatively, when the content of the aluminate is increased, the amount of calcium hypochlorite formed increases correspondingly when dissolved.

Assistants in the form of aluminum sulfate and sodium aluminate are typically used as coagulants. The concentration of the coagulant as aluminum oxide in a chemical agent is used as an indicator of the coagulating ability of these coagulants. Furthermore, concentration as aluminum oxide A can be determined using the formula indicated below:

$$A = 1.8895 \times a \quad \text{[Equation 1]}$$

(wherein, a represents the aluminum concentration (%) in the chemical agent as determined by titration and ICP-atomic emission spectroscopy, and 1.8895 is the conversion coefficient for $Al_2O_3/Al_2$).

In one example of a commonly available product, for example, the concentration as aluminum oxide of solid aluminum sulfate is 17.3% by weight. The concentration as aluminum oxide of sodium aluminate is 53.6% by weight. In the case of obtaining the same coagulation effects, the amount of sodium aluminate used is only required to be about one-third the amount of solid aluminum sulfate.

There are no particular limitations on the usage form of the composition of the present invention. Examples of usage forms include powder, granules, tablets and pellets. Among these, a usage form molded by dry molding is preferable. Specific examples of dry molding methods include tableting and pelleting with a briquette machine.

A known tableting device, for example, can be used for pressure molding by tableting. Although there are no particular limitations on the tableting pressure, the pressure in the form of gauge pressure is normally 5 MPa to 70 MPa and preferably 10 MPa to 30 MPa. If tableting pressure is within these ranges, the tablets or pellets have adequate strength, do not break up storage, and a suitable amount is dissolved when dissolving.

Although there are no particular limitations on the shape of the tablet or pellet, specific examples of shapes include a disc, rectangle or cylinder. There are also no particular limitations on the size thereof, and cylindrical tablets, for example, can have a diameter of 50 mm to 70 mm and a height of 25 mm to 35 mm.

The composition of the present invention can also contain various types of additives as necessary, such as a scale preventing agent, dissolution rate adjuster, pH adjuster or vehicle. One type of these additives may be used alone or two or more types may be used in combination. Examples of additives include chlorinated isocyanurates such as trichloroisocyanuric acid, sodium dichloroisocyanurate or potassium dichloroisocyanurate, alkaline agents such as sodium hydroxide, sodium bicarbonate or calcium hydroxide, boron compounds such as boric acid, borax or sodium tetraborate, silicates such as sodium silicate, magnesium sulfate and alum.

The composition of the present invention can be added directly to a target pool or can be injected using a container as in FIG. 1, and is preferably injected using a container.

There are no particular limitations on the method used to dissolve the chemical agent. For example, pool return water may be allowed to flow in through one opening of a container having at least two openings, while water in which the chemical agent has been dissolved may be discharged from the other opening, or in the case of a container having only one opening, pool return water may be allowed to flow in through the opening, and after the container becomes full and the chemical agent is dissolved therein, the water in which chemical agent has been dissolved may be discharged through the same opening. The former method is more efficient and therefore preferable in the present invention.

There are no particular limitations on the structure of the container, and specific examples thereof include a packed column or packed tank used in the chemical industry and the like, and a chemical agent container described in, for example, Japanese Unexamined Patent Application Publication (Translation of PCT Application) No. H04-500171, Japanese Unexamined Patent Application Publication (Translation of PCT Application) No. H06-501418, Japanese Examined Patent Application, Second Publication No. S59-13890 or Japanese Unexamined Patent Application, First Publication No. H08-155465.

EXAMPLES

Although the following provides a more detailed explanation of the present invention by indicating examples thereof, the scope of the present invention is not limited by the following examples. Additions, omissions, substitutions and other modifications can be made to the configuration of the present invention without departing from the spirit or scope of the present invention.

Example 1

98.0 parts by weight of a calcium hypochlorite composition (75% by weight of calcium hypochlorite, 8.5% by weight of salt, 12.7% by weight of water, remainder: calcium chloride, calcium chlorate, calcium hydroxide, etc.), 1.0 part by weight of sodium aluminate and sodium metaphosphate were placed in a container-mounted mixer followed by mixing well by stirring with a stirrer. The mixture was then tableted with a pelletizer at a tableting pressure of 25 MPa to obtain cylindrical tablets (approximately 200 g) having a diameter of 70 mm and length of 20 mm.

Examples 2 and 3

Tablets were obtained in the same manner as Example 1 with the exception of changing to the component ratios shown in the following Table 1.

Comparative Examples 1 and 2

Tablets were obtained in the same manner as Example 1 with the exception of changing to the component ratios shown in the following Table 1.

Test Example

The Model N-30 Sterilizer manufactured by Nippon Soda Co., Ltd. was installed at an intermediate location of the circulation path of a 25 meter, 6-lane swimming pool having a circulating filtration mechanism, 8 kg of the tablets prepared in Examples 1 to 3 and Comparative Examples 1 and 2 were added to the aforementioned sterilizer, and the pool water was continuously circulated for 1 week for 10 hours per day followed by visually observing the dissolved state of the tablets in the container.

The results were evaluated with ○ in the case there was no dissolution residue present in the container or if present, was not of an amount that impaired continuous use of the container, or were evaluated with X in the case of a large amount of dissolution residue present in the container that was judged to impair continuous use of the container.

In addition, a black cross was suspended on a wall of the pool, a photograph of the water in the pool was taken with an underwater camera at a distance of 12.5 m from the black cross, and the presence or absence of clearing effects was judged based on whether or not there was improvement in the degree to which the black cross was able to be visualized.

Figure 2:
FIG. 2 shows a photograph taken from a location 12.5 meters from a black cross suspended on the wall of a pool before testing.
Figure 3:
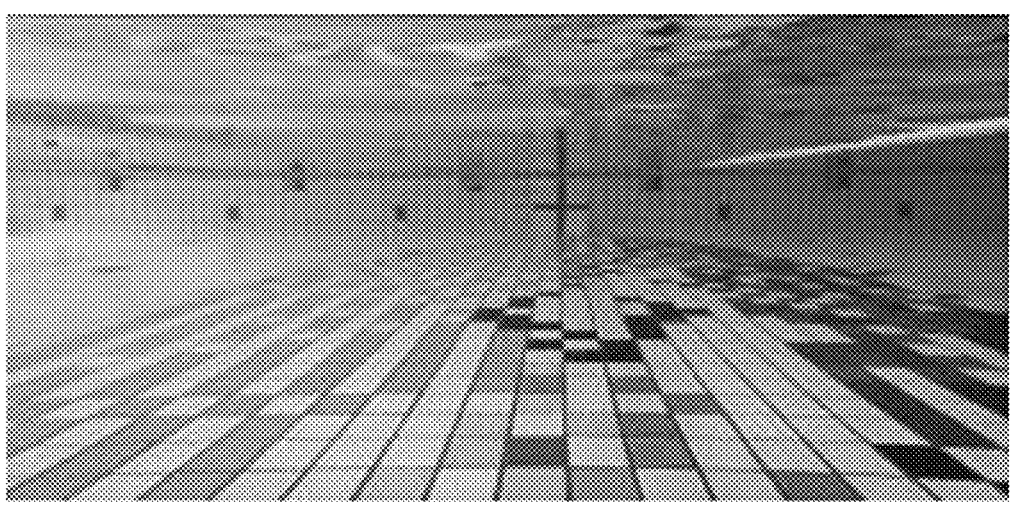
FIG. 3 shows a photograph taken from a location 12.5 meters from a black cross suspended on the wall of a pool after testing.

FIG. 2 shows a photograph taken before testing, while FIG. 3 shows a photograph taken after testing. In this manner, the results were evaluated with ○ in the case of improvement in the degree to which the black cross was able to be visualized before and after testing, or were evaluated with X in the case improvement was not observed or visibility worsened.

The results of the aforementioned testing are shown in Table 1.

TABLE 1

|  | Sodium aluminate content (wt %) | Dissolved state*1 | Clearness*2 |
|---|---|---|---|
| Example 1 | 1.0 | ○ | ○ |
| Example 2 | 1.2 | ○ | ○ |
| Example 3 | 1.5 | ○ | ○ |
| Comp. Ex. 1 | 0.5 | ○ | X |
| Comp. Ex. 2 | 2.0 | X | ○ |

INDUSTRIAL APPLICABILITY

The present invention is able to provide a composition that allows the obtaining of water clarity without causing clogging even in the case of using in a container installed at an intermediate location in a circulation path of a pool having a circulating filtration mechanism.

BRIEF DESCRIPTION OF THE REFERENCE SYMBOLS

1 Chemical agent dissolving tank
2 Main treated water pipe
3 Pipe for supplying water B
4 Perforated plate
5 Spray nozzle
6 Solid chemical agent addition port
7 Check valve (non-return valve)
8 Filtration pump
9 Filtration machine
10 Circulating water
11 Flow meter

The invention claimed is:

1. A composition comprising: an aluminate and calcium hypochlorite, and
   wherein the content of the aluminate is 1.0 part by weight to less than 2 parts by weight based on 100 parts by weight of the composition.

2. The composition according to claim 1, wherein the content of the aluminate is 1.0 part by weight to 1.5 parts by weight based on 100 parts by weight of the composition.

3. The composition according to claim 1, wherein the aluminate is sodium aluminate.

4. The composition according to claim 1, wherein the usage form of the composition is a tablet.

5. A method for producing a disinfectant comprising: dry molding a composition containing an aluminate and calcium hypochlorite, and
   wherein the content of the aluminate is 1.0 part by weight to less than 2 parts by weight based on 100 parts by weight of the composition.

6. The production method according to claim 5, wherein the dry molding consists of tableting, or consists of pelleting with a briquette machine.

* * * * *